US00PP25599P2

(12) United States Plant Patent
Nishikawa

(10) Patent No.: US PP25,599 P2
(45) Date of Patent: May 26, 2015

(54) ***DELOSPERMA* PLANT NAMED 'WOWDW7'**

(50) Latin Name: *Delosperma cooperi*
Varietal Denomination: WOWDW7

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 88 days.

(21) Appl. No.: 13/987,577

(22) Filed: Aug. 9, 2013

(51) Int. Cl.
*A01H 5/02* (2006.01)

(52) U.S. Cl.
USPC ..... Plt./422

(58) Field of Classification Search
CPC ..... A01H 5/00
USPC ..... Plt./422
See application file for complete search history.

(56) References Cited

PUBLICATIONS

CPVO, Feb. 2013.*

* cited by examiner

*Primary Examiner* — June Hwu
*Assistant Examiner* — Keith Robinson
(74) *Attorney, Agent, or Firm* — Penny J. Aguirre

(57) ABSTRACT

A new cultivar of *Delosperma* plant, 'WOWDW7', characterized by its compact and horizontal plant habit, its very floriferous and long blooming flowering habit, and its large flowers with white petals and white petaloids.

2 Drawing Sheets

Botanical classification: *Delosperma cooperi.*
Variety denomination: 'WOWDW7'.

CROSS REFERENCE TO RELATED APPLICATIONS

This application is co-pending with U.S. Plant Patent Applications filed for plants derived from the same breeding program that are entitled *Delosperma* Plant Named 'WOWDOY3' (U.S. Plant patent application Ser. No. 13/987,585), *Delosperma* Plant Named 'WOW2011-1' (U.S. Plant patent application Ser. No. 13/987,575), *Delosperma* Plant Named 'WOWDRY1' (U.S. Plant patent application Ser. No. 13/987,588), *Delosperma* Plant Named 'WOWDAY2' (U.S. Plant patent application Ser. No. 13/987,587), and *Delosperma* Plant Named 'WOWDRW5' (U.S. Plant patent application Ser. No. 13/987,584).

BACKGROUND OF THE INVENTION

The present invention relates to a new and distinct cultivar of *Delosperma* plant, botanically known as *Delosperma cooperi* 'WOWDW7' and will be referred to hereinafter by its cultivar name, 'WOWDW7'. The new cultivar of *Delosperma* is an herbaceous perennial grown for container and landscape use.

The new cultivar was derived from a controlled breeding program conducted by the Inventor in Ichinimiya-City, Aichi-Pref, Japan. The overall purpose of the breeding program was to develop new cultivars of *Delosperma* plants with low-growing and well-spreading growth habits combined with long flowering periods and a unique range of flower colors.

'WOWDW7' was selected in the Inventor's trial garden in summer of 2011 as a single unique plant from amongst the seedlings derived from self crossing an unnamed plant from the Inventor's breeding program, ref. code HANADW1002, in summer of 2010.

Asexual propagation of the new cultivar was first accomplished by softwood stem cuttings in summer of 2011 by the Inventor in Ichinimiya-City, Aichi-Pref, Japan. Asexual propagation by softwood stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'WOWDW7' as a unique cultivar of *Delosperma.*

1. 'WOWDW7' exhibits a compact and horizontal plant habit.
2. 'WOWDW7' exhibits a very floriferous and long blooming flowering habit; blooming about 8 months.
3. 'WOWDW7' exhibits large flowers with white petals and white petaloids.

The parent plant of 'WOWDW7', ref. code HANADW1002, differs from 'WOWDW7' in having a taller plant habit, in blooming for a shorter time period, and in having smaller flowers. 'WOWDW7' can be most closely compared to the cultivar 'Jewel of Desert Garnet' (U.S. Plant Pat. No. 23,471), which is similar to 'WOWDW7' in having a horizontal plant habit. 'Jewel of Desert Garnet' differs from 'WOWDW7' in having smaller flowers that have pink on the lower portion of the petals and pink petaloids, in having a shorter bloom period, and in having a shorter plant height. 'WOWDW7' can also be compared to cultivars with co-pending patent applications from the same breeding program and are similar in plant height and in having large flowers.

'WOWDRY 1' has flowers with petals that are magenta pink on the outer region and yellow and white towards the center of the flower surrounding yellow and white petaloids.

'WOW2011-1' has flowers with yellow petals and yellow petaloids.

'WOWDAY2' has flowers with petals that are red on the outer region and yellow towards the center of the flower surrounding yellow petaloids.

'WOWDRW5' has flowers with petals that are magenta pink on the outer region and white towards the center of the flower surrounding white petaloids.

'WOWDOY3' has flowers with petals that are orange on the outer region and yellow towards the center of the flower surrounding yellow petaloids.

BRIEF DESCRIPTION OF THE DRAWINGS

The accompanying colored photographs illustrate the overall appearance and distinct characteristics of the new *Delosperma*. The plant in the photograph is 3 months in age as grown in a 9-cm container in an unheated greenhouse in Noordwijkerhout, The Netherlands.

The photograph in FIG. 1 provides a side view of 'WOWDW7' in bloom.

Figure 1:
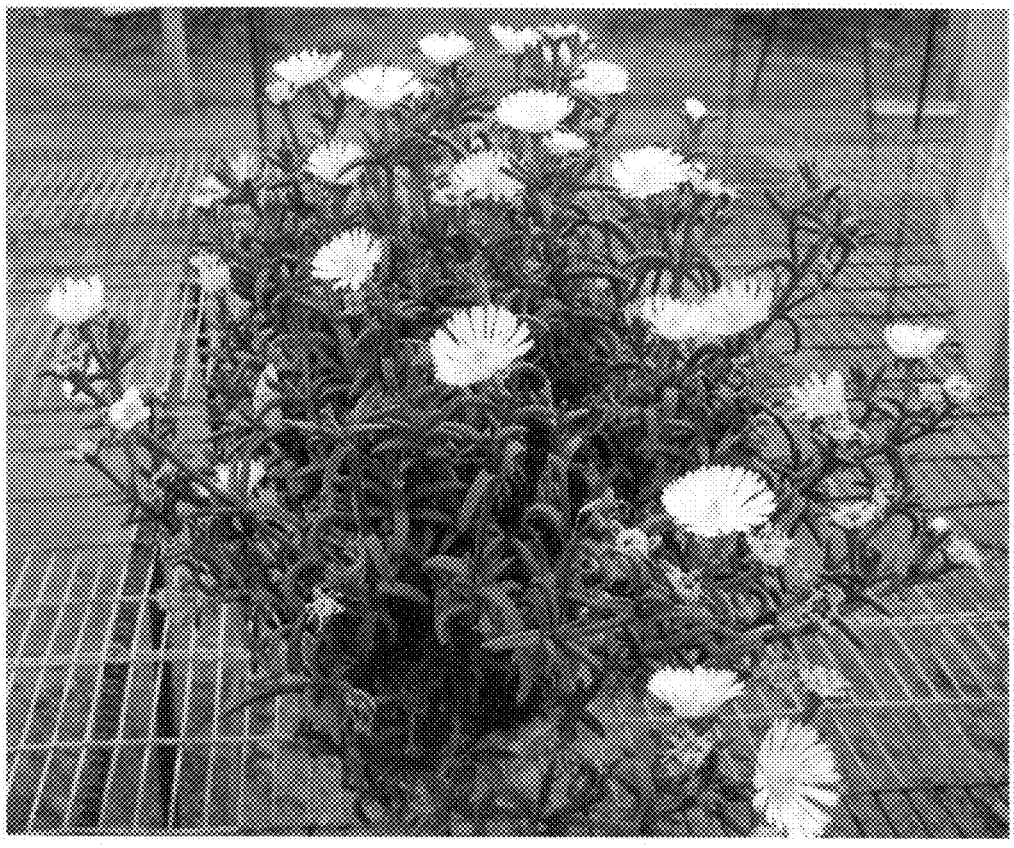
Figure 2:
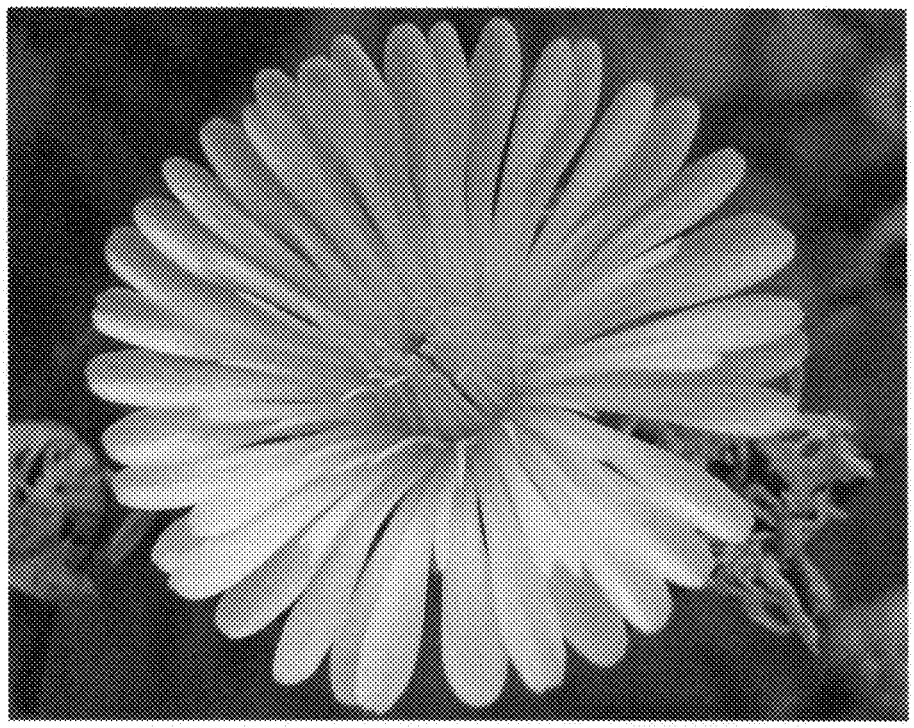

The photograph in FIG. 2 provides a close-up view of a flower of 'WOWDW7'.

Figure 3:
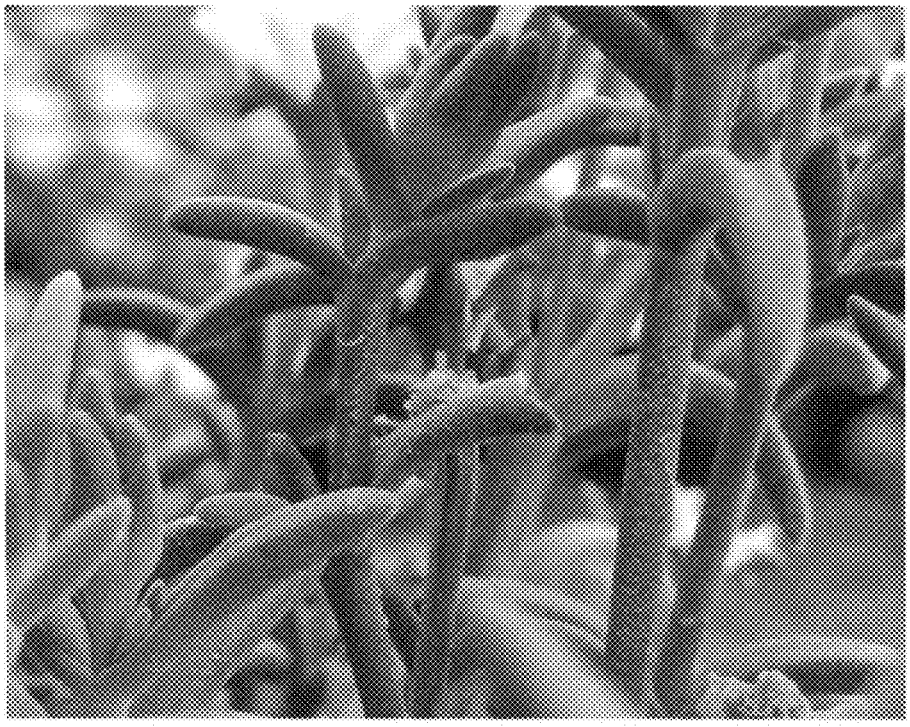

The photograph in FIG. 3 provides a close-up view of the foliage of 'WOWDW7'.

The colors in the photograph may differ slightly from the color values cited in the detailed botanical description, which accurately describe the colors of the new *Delosperma*.

DETAILED BOTANICAL DESCRIPTION

The following is a detailed description of 3 months-old plants of the new cultivar as grown in 9-cm containers in an unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from spring to late summer fall for approximately 8 months in The Netherlands.

*Plant type.*—Herbaceous perennial.

*Plant habit.*—Flattened, prostrate.

*Height and spread.*—Reaches an average of 17.3 cm in height and about 26.2 cm in diameter.

*Cold hardiness.*—Observed to be hardy to at least U.S.D.A. Zone 7.

*Diseases.*—No more susceptible to diseases than other *Delosperma cooperi* varieties.

*Root description.*—No root structures.

*Propagation.*—Softwood stem cuttings.

*Growth habit.*—Moderate.

Stem description:

*Shape.*—Round.

*Stem color.*—Young stems; 145C upper side strongly tinged with 184B to 184C, older stems; 196C to 196D.

*Stem size.*—Lateral branches; an average of 13.8 cm in length and 2.5 mm in diameter.

*Internode length.*—An average of 3.4 mm.

*Stem substance.*—Succulent.

*Stem strength.*—Low.

*Stem surface.*—Moderately glossy, moderately pubescent with very short glandular hairs; an average of 0.2 mm in length and closest to 155C in color.

*Branching habit.*—Freely branching both basal and lateral, an average of 11 lateral branches per stem.

Foliage description:

*Leaf shape.*—Ligulate, triangular in diameter.

*Leaf substance.*—Succulent.

*Leaf division.*—Simple.

*Leaf base.*—Cuneate.

*Leaf apex.*—Acute.

*Leaf venation.*—No veins visible.

*Leaf margins.*—Entire.

*Leaf arrangement.*—Opposite.

*Leaf surface* (*upper and lower surface*).—Slightly glossy, sparsely to moderately pubescent with very short glandular hairs; an average of 0.2 mm in length, 157D in color.

*Leaf color.*—Young upper surface 138A to 138B and lower surface; 138B, mature upper surface 137A to 137B and lower surface; 137B.

*Leaf size.*—About 2.8 cm in length and 4 mm in width.

*Leaf quantity.*—Average of 10 (5 pairs) per lateral branch.

*Leaf attachment.*—Sessile.

Inflorescence description:

*Inflorescence type.*—Flowers solitary, terminal.

*Flower number.*—An average of 1 per lateral stem, 77 per plant in a 9-cm container.

*Flower fragrance.*—Faint, sweet and pleasant.

*Flower aspect.*—Outward to upright.

*Flower longevity.*—An average of 4 days, self-cleaning.

*Flower type.*—Single.

*Flower size.*—Average of 3.2 cm in diameter and 9 mm in depth.

*Flower buds.*—Broadly ovate to oblong in shape, an average of 1 cm in length and 5 mm in diameter, color; 138B with base 145B, surface texture is smooth and glossy with the sepal portion smooth and slightly glossy.

*Calyx.*—Rotate in shape, an average of 5 mm in depth and 1.6 cm in diameter.

*Sepals.*—5, rotate, ovate in shape, margin entire, an average of 7 mm in length and 3 mm in width, broadly acute apex, broadly cuneate base, surface is smooth and slightly glossy on upper and lower surface, color young upper and lower surface; 138B, base 145B, color mature upper and lower surface; 143B.

*Petals.*—An average of 40 per flower, rotate and slightly curved downward, narrowly oblanceolate in shape, surface is smooth and glossy on both surfaces, margin entire, apex obtuse, base truncate, an average of 1.4 cm in length and 2 mm in width, color; opening flowers upper and lower surface; NN155C to NN155D, base NN155A, fully opened flower upper and lower surface; NN155C to NN155D, base NN155B, non fading.

*Petaloids.*—An average of 30 per flower, rotate and near vertical surrounding stamens, lanceolate in shape, glabrous and moderately to highly glossy on both surfaces, margin entire, apex acute, base truncate, an average of 6 mm in length and 1 mm in width, color immature and mature upper and lower surface; NN155A to NN155B.

*Peduncle.*—An average of 1.6 cm in length and 1.5 mm in diameter, straight on top of lateral branch at 0°, weak in strength, color; a blend between 144C and 145B, surface texture is moderately glossy and moderately pubescent.

*Pedicel.*—None.

Reproductive organs:

*Pistils.*—An average of 5, 2 mm in length, stigma triangular shaped (pointed), style and stigma (not distinguishable) and combined an average of 2 mm in length and 144A in color, ovary is 143C in color.

*Stamens.*—Average 60, 12A in color, anthers are dorsifixed and narrowly oblong in shape, an average of 0.8 mm in diameter, filaments are 3 mm in length 11D in color, pollen is moderate to high in quantity and 6A in color.

*Fruit.*—Fruit and seed production was not observed under the conditions tested.

It is claimed:

1. A new and distinct variety of *Delosperma* plant named 'WOWDW7' as described and illustrated herein.

* * * * *